United States Patent [19]

Godtfredsen et al.

[11] Patent Number: 5,534,435
[45] Date of Patent: Jul. 9, 1996

[54] PROCESS FOR DECOMPOSING PEROXYCARBOXYLIC ACIDS

[75] Inventors: Sven E. Godtfredsen, Værløse; Ole Kirk; Ture Damhus, both of Copenhagen, all of Denmark

[73] Assignee: Novo Nordisk A/S, Bagsvaerd, Denmark

[21] Appl. No.: 390,351

[22] Filed: Feb. 8, 1995

Related U.S. Application Data

[63] Continuation of Ser. No. 946,998, Sep. 17, 1992, filed as PCT/DK91/00084, Mar. 19, 1991, abandoned.

[30] Foreign Application Priority Data

Mar. 20, 1990 [DK] Denmark .................................. 0714/90

[51] Int. Cl.$^6$ ....................................................... C12P 7/40
[52] U.S. Cl. ........................................ 435/262.5; 435/136
[58] Field of Search ............................... 435/262.5, 136, 435/197-8

[56] References Cited

U.S. PATENT DOCUMENTS 5,168,655   12/1992   Davidson et al. ............................ 47/62

OTHER PUBLICATIONS

Jensen et al. "Lipolase:A Microbial Lipose for Detergents Developed by Application of R–DNA Technique," Commun. Jorn. Con. Esp. Deterg. vol. 21 (1990) pp. 23–37.

Bjorkling et al. "Lipase–Mediated Formation of Peroxycarboxylic Acids Used in Catalytic Epoxidation of Alkenes." J. Chem. Soc., Chem. Comm, 1990 pp. 1301–1303.

Jones et al., J. Biochem., vol. 143, No. 2, pp. 473–474 (1974).

Araiso et al., Can. J. Biochem. vol. 59, No. 4, pp. 233–236 (1981).

Palcic et al., J. Biol. Chem., vol. 255, No. 13, pp. 6128–6132 (1981).

*Primary Examiner*—Esther M. Kepplinger
*Assistant Examiner*—T. J. Reardon
*Attorney, Agent, or Firm*—Steve T. Zelson; Elias J. Lambiris

[57] ABSTRACT

The invention relates to a process for converting peroxycarboxylic acids to carboxylic acids, the process comprising treating a peroxycarboxylic acid of the general formula I:

$$R-CO-OOH \qquad (I)$$

wherein R is a linear or branched alkyl group, an aryl group or an aryl-alkyl group each of which may optionally be substituted with one or more hydroxy, halogen, alkoxy, amino, alkylamino, sulfo, sulfoxy, sulfono, amido, carboxy, percarboxy or nitro groups, with an enzyme catalyst to form the corresponding carboxylic acid of the general formula II:

$$R-CO-OH \qquad (II)$$

wherein R has the meaning indicated above.

7 Claims, No Drawings

PROCESS FOR DECOMPOSING PEROXYCARBOXYLIC ACIDS

CROSS-REFERENCE TO RELATED APPLICATION

This application is a continuation of co-pending application Ser. No. 07/946,998, filed Sep. 17, 1992, now abandoned, which is a continuation-in-part of PCT/DK91/00084 filed Mar. 19, 1991, which is incorporated herein by reference.

FIELD OF INVENTION

The present invention relates to a process for decomposing peroxycarboxylic acids by treatment with a catalyst.

BACKGROUND OF THE INVENTION

Peroxycarboxylic acids constitute an important class of substances which may be used for a wide range of purposes. Thus, peroxycarboxylic acids are commonly employed as oxidizing reagents in the field of organic synthesis for the production of a variety of organic chemicals. In particular, organic molecules containing unsaturations or other reducing groups may be oxidized in a high yield under mild conditions when subjected to peroxycarboxylic acids during organic synthesis, and consequently peroxycarboxylic acids may advantageously be used, e.g., for the preparation of epoxides from unsaturated hydrocarbons. Apart from their use as oxidation reagents, peroxycarboxylic acids may also be used as bleaching agents, for instance to decolorize paper mill process streams. Furthermore, preparations of peroxycarboxylic acids may be used for disinfection purposes (e.g. in the food industry) due to the sensitivity of microorganisms to these compounds (see e.g. H. C. Flemming, Zbl. Bakt. Hyg., I.Abt.Orig. B 179, 97–111 (1984)).

While peroxycarboxylic acids are highly advantageous reagents for these and other applications, their continued presence in the end products is not always desirable as they represent a potential environmental or health hazard. For instance, solutions of dyes decolorized by means of peroxycarboxylic acids should preferably be free from remaining peroxycarboxylic acid before being discharged into the environment where the peroxycarboxylic acid might exert a harmful effect. Similarly, utensils and surfaces disinfected in the food industry by means of peroxycarboxylic acids should be free from the reagent prior to use since the peroxycarboxylic acid may otherwise deteriorate the food product produced or eventually reach the consumer. Furthermore, substances prepared by chemical synthesis utilizing peroxycarboxylic acids should be free from the oxidation reagent which for instance might undesirably influence the further use or conversion of the synthesized substance.

Accordingly, there is a need for processes whereby residual peroxycarboxylic acids may be removed, in particular processes which allow for selective decomposition of peroxycarboxylic acids under mild conditions and which may thus be applied for the removal of peroxycarboxylic acids without adversely affecting other components in the peroxycarboxylic acid containing medium. Such processes should preferably also be economically viable for the treatment of large volumes of very dilute peroxycarboxylic acid containing solutions. To the present inventors' knowledge, no entirely satisfactory processes for the removal of peroxycarboxylic acids are currently available, and the use of peroxycarboxylic acids is accordingly limited, no matter how desirable their application in many processes may be.

SUMMARY OF THE INVENTION

It has surprisingly been found that certain enzymes may advantageously be used for the conversion of peroxycarboxylic acids to the corresponding carboxylic acids. Such enzymatic processes permit selective transformation of peroxycarboxylic acids under mild conditions and provide an economical way of removing peroxycarboxylic acids from large volumes of dilute solutions of the peroxycarboxylic acids.

Accordingly, the present invention relates to a process for converting peroxycarboxylic acids to carboxylic acids, the process comprising treating a peroxycarboxylic acid of the general formula I:

$$R\text{—}CO\text{—}OOH \quad (I)$$

wherein R is a linear or branched alkyl group, an aryl group or an aryl-alkyl group each of which may optionally be substituted with one or more hydroxy, halogen, alkoxy, amino, alkylamino, sulfoxy, sulfono, amido, carboxy, percarboxy or nitro groups, with an enzyme catalyst to form the corresponding carboxylic acid of the general formula II:

$$R\text{—}CO\text{—}OH \quad (II)$$

The use of enzymes (especially hydrolases) has previously been proposed for the formation of peroxycarboxylic acids in aqueous solutions. Thus German Patent 2 240 605 (Colgate-Palmolive Co.) suggests the use of hydrolases, in particular esterases or lipases of plant or animal origin, for generating peroxycarboxylic acids from simple ester substrates. Likewise the use of lipases in general and a lipase derived from *Pseudomonas putida* in particular for generating peroxycarboxylic acids from ester substrates is described in EP 253 487 and EP 268 456 (both to Clorox). A similar use of proteases is described in EP 310 952 (Henkel). To the best of the present inventors' knowledge, however, it has not previously been proposed to degrade peroxycarboxylic acids by means of such enzymes.

DETAILED DESCRIPTION OF THE INVENTION

Enzymes which may be employed as catalysts in the process of the invention are preferably hydrolases such as proteases, esterases and lipases. From the point of view of cost and availability it is advantageous to employ enzymes producible by microorganisms such as yeasts, bacteria or fungi.

Lipases which may be employed in the present process may be microbial lipases produced, for instance, by strains of Aspergillus, Enterobacterium, Chromobacterium, Geotricium or Penicillium. Preferred lipases for use according to the invention are those produced by species of Aspergillus, Mucor, Humicola, Pseudomonas or Candida.

Particularly preferred lipases are those produced by the following strains of microorganisms:

*Humicola lanuginosa*, DSM 3819 and 4109,

*Humicola brevispora*, DSM 4110,

*Humicola brevis* var. *thermoidea*, DSM 4111, and

*Humicola insolens*, DSM 1800.

To produce the lipase, the strain producing the enzyme may be cultivated under aerobic conditions in a nutrient medium containing assimilable carbon and nitrogen sources as well as essential minerals, trace elements etc., the medium being composed according to established practice. After cultivation, liquid enzyme concentrates may be prepared by removing insoluble materials, e.g. by filtration or centrifugation, after which the culture broth may be concentrated by evaporation or reverse osmosis. Solid enzyme preparations may be prepared from the concentrate by precipitation with salts or water-miscible solvents, e.g. ethanol, or by drying such as spray-drying in accordance with well-known methods.

Other lipases which may be used in the process of the invention are commercial lipases, e.g., those known under the trade names PALATASE® (a lipase obtainable from *Aspergillus niger*, available from Novo Nordisk A/S) and LIPOLASE™ (a recombinant fungal lipase produced by use of *Aspergillus oryzae*, also obtainable from Novo Nordisk A/S).

The lipase may furthermore be one producible by recombinant DNA techniques, cf. for instance EP 238 023.

The esterase employed in the process of the invention may be of animal or microbial origin. A suitable esterase for the present purpose is one obtainable from hog liver.

When employed in the process of the invention, the enzyme may be in a soluble state. It is, however, preferred to immobilize the enzyme on a solid support in order to facilitate the separation of the enzyme from the material treated with peroxycarboxylic acid. Immobilization procedures are well known (cf. for instance K. Mosbach, ed., "Immobilized Enzymes" *Methods in Enzymology* 44, Academic Press, New York, 1976) and include cross-linking of cell homogenates, covalent coupling to insoluble organic or inorganic supports, entrapment in gels and adsorption to ion exchange resins or other adsorbent materials. Coating on a particulate support may also be employed (cf. for instance A. R. Macrae and R. C. Hammond, *Biotechnology and Genetic Engineering Reviews* 3, 1985, p. 193). Suitable support materials for the immobilized enzyme are, for instance, plastics (e.g. polypropylene, polystyrene, polyvinylchloride, polyurethane, latex, nylon, polytetrafluoroethylene, polyethylene terephthalates, polyvinylacetate, polyvinylalcohol or any suitable copolymer thereof), polysaccharides (e.g. agarose or dextran), ion exchange resins (both cation and anion exchange resins), silicon polymers (e.g. siloxane) or silicates (e.g. glass).

It is preferred to immobilize the enzyme on an ion exchange resin by adsorbing the enzyme to the resin or by cross-linking it to the resin by means of glutaraldehyde or another cross-linking agent in a manner known per se. A particularly preferred resin is a weakly basic anion exchange resin which may be a polystyrene-, acrylic- or phenol-formaldehyde-type resin. Examples of commercially available resins are LEWATIT E 1999/85 or E2001/85 (registered trademark of Bayer, Federal Republic of Germany) and DUOLITE ES-568 (registered trademark of Rohm & Haas, FRG). Immobilization of enzymes to acrylic-type resins may be carried out according to EP 140 542. Immobilization to phenol-formaldehyde-type resins may be done according to DK 85/878.

Another convenient material for immobilizing enzymes is an inorganic support, such as a silicate. The enzyme may be attached to the support by adsorption or by covalent coupling, e.g. as described in K. Mosbach, ed., op. cit.

R in the general formulae I and II above is preferably a linear alkyl group, in particular a linear alkyl group with 1–19 carbon atoms, preferably 1–13 carbon atoms, more preferably 1–10 carbon atoms and most preferably 2 or 8–10 carbon atoms. R may also be an alkyl group substituted by one or more halogen atoms, preferably chloro atoms.

According to the invention, the conversion of the peroxycarboxylic acid (I) to the carboxylic acid (II) may be carried out in an aqueous medium. This is an advantage when the peroxycarboxylic acid treatment preceding the present process takes place in, for instance, an aqueous solution, such as a solution of pigments or a solution of peroxycarboxylic acid used for disinfection purposes.

The process of the invention is particularly useful in connection with bleaching processes, disinfection processes and organic synthesis processes involving the use of peroxycarboxylic acids. In these instances any peroxycarboxylic acid remaining after the oxidation process may conveniently be removed by treatment with the enzyme catalyst. Since enzymes exhibit a high affinity for their substrates (in this case the peroxycarboxylic acids) and a high degree of specificity, the conversion of the peroxycarboxylic acid may be carried out substantially without affecting any other compounds present, and may furthermore be used to remove even small amounts of peroxycarboxylic acid.

Accordingly, the process of the present invention may suitably be employed for the conversion of the peroxycarboxylic acid (I) or residues thereof to the carboxylic acid (II) in a step subsequent to disinfecting an object (e.g. a utensil or a surface) with the peroxycarboxylic acid (I). In another favored embodiment, the process of the invention may be employed for the conversion of the peroxycarboxylic acid (I) or residues thereof to the carboxylic acid (II) in a subsequent step to bleaching a colored substance with the peroxycarboxylic acid (I). In yet another favored embodiment, the process of the invention may be employed for the conversion of the peroxycarboxylic acid (I) or residues thereof to the carboxylic acid (II) in a subsequent step to the oxidation of organic or inorganic substrates with a peroxycarboxylic acid (I).

Certain enzymes, when employed according to the invention, will give rise to the formation of hydrogen peroxide concomitantly with conversion of the peroxycarboxylic acid as shown in Reaction Scheme 1 below in which R has the meaning indicated above:

Reaction Scheme 1

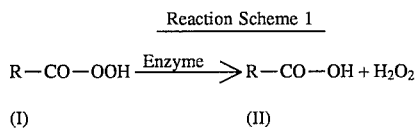

(I)   (II)

In some cases, it may be advantageous to convert the hydrogen peroxide formed in the reaction with an enzyme with a view to removing this oxidizing species from the reaction mixture or initiating oxidizing processes in the reaction medium, based on the use of hydrogen peroxide. Accordingly, it may be advantageous to carry out the conversion of the peroxycarboxylic acid (I) in the presence of a hydrogen peroxide converting enzyme or, alternatively, to subject the hydrogen peroxide formed as a result of the conversion of the peroxycarboxylic acid (I) to subsequent treatment with a hydrogen peroxide converting enzyme. Examples of suitable hydrogen peroxide converting enzymes are catalase, peroxidases, and haloperoxidases.

The process of the invention is further illustrated by the following examples which are not intended to be in any way limiting to the scope of the invention as claimed.

EXAMPLES

General Methods

Peroxycarboxylic acids were prepared according to the method described by W. E. Parker, C. Ricciuti, C. L. Ogg and D. Swern, J. Am. Chem. Soc. 77, 4037 (1955) except for peracetic acid which was obtained as an approximately 2 M solution under the trademark Proxitane 507. Peroxycarboxylic acid levels may be determined, also when hydrogen peroxide is present together with the peroxycarboxylic acid, by methods known in the art, e.g. by iodometry at 5° C. as described by Sully and Williams in *Analyst*, 1962, 87, 653 (this method also gives the concentration of hydrogen peroxide). One Lipase Unit (LU) is the amount of enzyme which liberates one micromole of butyric acid per minute from tributyrin as a substrate in a pH-stat at 30° C. and pH 7 (a detailed description of the assay (AF 95) is available from Novo Nordisk A/S upon request).

Example 1

To a 0.47 mM solution of peroctanoic acid in a 50 mM phosphate buffer at pH 7 and 40° C. was added 10 LU/ml PALATASE® (a fungal lipase produced by fermentation of a strain of *Aspergillus niger*), and the peroxycarboxylic acid concentration was monitored as a function of time (the numbers in brackets refer to a reference-experiment performed under similar conditions but without addition of enzyme):

| Time | Peracid concentration (mM) |
| --- | --- |
| Before addition of enzyme | 0.47 (0.50) |
| 3 min | 0* (0.50) |
| 9 min | 0* (0.48) |

*)Not detectable.

Example 2

To a 0.56 mM solution of peracetic acid in a 50 mM phosphate buffer at pH 7 and 40° C. was added 10 LU/ml PALATASE® (as described in example 1) and the peroxycarboxylic acid concentration was monitored as a function of time:

| Time after addition of enzyme (min) | Peracid concentration (mM) |
| --- | --- |
| 0 | 0.56 |
| 4 | 0.26 |
| 9 | 0.08 |
| 14 | 0 (not detectable) |

In a similar experiment, but without any addition of enzyme, the peroxycarboxylic acid concentration declined much more slowly as shown in the following table:

| Time (min) | Peracid concentration (mM) |
| --- | --- |
| 0 | 0.61 |
| 5 | 0.57 |
| 10 | 0.55 |
| 15 | 0.53 |

Example 3

To a 0.2 mM solution of peracetic acid in a 50 mM phosphate buffer pH 8 and 25° C. was added 50 U/ml (Sigma units) Esterase from Hog Liver (Sigma E-3128, 6365 U/ml) and the peroxycarboxylic acid concentration was monitored as a function of time:

| Time after addition of enzyme (min) | Peracid concentration (mM) |
| --- | --- |
| 0 | 0.20 |
| 2 | 0.15 |
| 10 | 0 (not detectable) |
| 18 | 0 (not detectable) |

In a corresponding experiment with no enzyme, the peracetic acid concentration did not change within 18 min.

Example 4

To a solution of 0.5 mM pernonanoic acid in 15 mM phosphate buffer at pH 8.5 and 22° C. was added 5 LU/ml LIPOLASE™ (available from Novo Nordisk A/S) and both the peroxycarboxylic acid concentration and the concentration of $H_2O_2$ was monitored as a function of time:

| | Concentrations (mM) | |
| --- | --- | --- |
| Time | Pernonanoic acid | $H_2O_2$ |
| Immediately after addition of enzyme | 0.30 | 0.08 |
| 13 min later | 0 (not detectable) | 0.32 |

In a corresponding experiment with no enzyme, the peroxycarboxylic acid concentration was unchanged after 14 min.

The following two examples demonstrate the removal of peracids with an immobilized enzyme, LIPOZYME™, available from Novo Nordisk A/S. This product is based on a fungal lipase produced by fermentation of a strain of *Mucor miehei* and immobilized on a macroporous anion exchange resin.

Example 5

A 0.5 mM solution of pernonanoic acid was prepared in a 50 mM sodium phosphate buffer at pH 8.4. The stirred solution was thermostated at 30° C. and the pernonanoic acid level monitored for 30 min, during which time no decrease was observed. Then a preparation of LIPOZYME™ was added to the peracid solution to 1 g/l. Further observation of pernonanoic acid levels showed a fast decrease (LIPOZYME™ added at 0 min):

| Time (min) | Pernonanoic acid (%, 100% = 0.5 mM) |
| --- | --- |
| 0 | 100 |
| 6 | 39 |
| 12 | 5 |
| 18 | 6 |
| 24 | not detectable |
| 30 | not detectable |

Example 6

Stirred solutions of peracetic acid were prepared in 3 different media:

Solution 1: 100 mM sodium acetate, pH=4.0, temperature 30° C.

Solution 2: 50 mM sodium phosphate, pH=6.9, temperature 30° C.

Solution 3: 50 mM sodium phosphate, pH= 8.0, temperature 30° C.

After measuring the initial level of peracetic acid, which was in all cases between 1.1 and 1.3 mM, LIPOZYME™ was added to 1 g/l in each solution and peracetic acid followed as a function of time.

The following was observed:

| | Peracetic acid concentration (%) | | |
|---|---|---|---|
| Time (min) | Solution 1 | Solution 2 | Solution 3 |
| 0 | 100 | 100 | 100 |
| 6 | 85 | 77 | 85 |
| 12 | 64 | 64 | not measured |
| 18 | 50 | 49 | 50 |
| 24 | 35 | 39 | 43 |
| 30 | 29 | 30 | 24 |

In control experiments without LIPOZYME™, the decrease in peracid concentration was in all cases less than 6% during a 30 min observation period.

We claim:

1. A process for converting a peroxycarboxylic acid to the corresponding carboxylic acid, wherein the peroxycarboxylic acid is of formula I:

R—CO—OOH (I)

wherein

R is a linear or branched alkyl group, an aryl group or an aryl-alkyl group, each of which may optionally be substituted with one or more hydroxy, halogen, alkoxy, amino, alkylamino, sulfo, sulfoxy, sulfono, amido, carboxy, percarboxy or nitro groups; comprising treating the peroxycarboxylic acid with an enzyme selected from the group consisting of esterase and lipase in an aqueous medium at suitable conditions.

2. The process according to claim 1, wherein the enzyme is a lipase.

3. The process according to claim 2, wherein the enzyme is a microbial lipase.

4. The process according to claim 3, wherein the source of the lipase is a strain of Mucor, Aspergillus, Humicola, Pseudomonas or Candida.

5. The process according to claim 1, wherein the enzyme is immobilized on a solid support.

6. The process according to claim 1, wherein R is a linear alkyl group with 1–19 carbon atoms.

7. The process according to claim 6, wherein the alkyl group is substituted with one or more halogen atoms.

* * * * *